United States Patent [19]
Uehara et al.

[11] Patent Number: 5,592,216
[45] Date of Patent: Jan. 7, 1997

[54] ENDOSCOPIC APPARATUS CAPABLE OF STORING IMAGE INFORMATION FOR A PLURALITY OF FRAMES

[75] Inventors: Masao Uehara, Hachioji; Katsuyuki Saito, Kokubunji; Akinobu Uchikubo, Ōme; Takehiro Nakagawa, Hachioji; Masahiko Sasaki, Hachioji; Shinji Yamashita, Hachioji, all of Japan

[73] Assignee: Olympus Optical Co., Ltd., Tokyo, Japan

[21] Appl. No.: 294,207

[22] Filed: Aug. 22, 1994

Related U.S. Application Data

[63] Continuation of Ser. No. 106,692, Aug. 16, 1993, abandoned, which is a continuation of Ser. No. 788,678, Nov. 6, 1991, abandoned.

[30] Foreign Application Priority Data

Nov. 9, 1990 [JP] Japan ................................ 2-305516

[51] Int. Cl.$^6$ ........................... A61B 1/04; H04N 7/18
[52] U.S. Cl. ................................. 348/74; 348/75
[58] Field of Search ......................... 348/24, 75, 565, 348/718, 719, 552, 65; 361/685

[56] References Cited

U.S. PATENT DOCUMENTS

| 4,755,873 | 7/1988 | Kobayashi | 358/98 |
|---|---|---|---|
| 5,006,928 | 4/1991 | Kawajiri et al. | 358/98 |
| 5,061,994 | 10/1991 | Takahashi | 358/98 |
| 5,111,306 | 5/1992 | Kanno et al. | 348/74 |
| 5,124,789 | 6/1992 | Hiyama et al. | 348/74 |
| 5,134,484 | 7/1992 | Willson | 348/565 |
| 5,153,721 | 10/1992 | Eino et al. | 348/74 |
| 5,176,523 | 1/1993 | Lai | 361/685 |

FOREIGN PATENT DOCUMENTS

| 51-65962 | 6/1976 | Japan . |
|---|---|---|
| 55-54933 | 4/1980 | Japan . |

Primary Examiner—Victor R. Kostak
Attorney, Agent, or Firm—Armstrong, Westerman, Hattori, McLeland & Naughton

[57] ABSTRACT

The present invention relates to an endoscopic apparatus which creates image information based on picture signals from an electron endoscope and has a memory device for storing the image information. The endoscopic apparatus is provided with a driver for driving a solid-state image pickup device in the endoscope, a picture signal generation circuit for generating a picture signal based on an image pickup signal which is photoelectrically converted by the solid-state image pickup device, an A/D conversion circuit for converting the picture signal from analog to digital, a process circuit for creating image information to be transferred to a memory capable of storing image information for one frame, based on the picture signal by digital processing, such as interpolation, a small capacity memory capable of storing image information for a plurality of frames and composed of, for example, a semiconductor, a CPU for controlling writing/ reading between the memory and the small capacity memory, and a D/A conversion circuit for converting the image information from digital to analog so as to generate a video picture signal.

19 Claims, 9 Drawing Sheets

ENDOSCOPIC APPARATUS CAPABLE OF STORING IMAGE INFORMATION FOR A PLURALITY OF FRAMES

This application is a continuation of application Ser. No. 08/106,692, filed Aug. 16, 1993, now abandoned, which is a continuation of application Ser. No. 08/788,678, filed Nov. 6, 1991, now abandoned.

BACKGROUND OF THE INVENTION

1. Field of the Invention

The present invention relates to an endoscopic apparatus and more particularly, to an endoscopic apparatus which creates image information based on an image pickup signal from an electronic endoscope and which has a memory means for retaining the image information.

2. Description of the Related Art

Various kinds of endoscopes each using a solid-state image pickup device, such as a CCD (Charge-Coupled Device), have been recently proposed.

In such an endoscope, color image information is obtained in the following two methods: One is the simultaneous method in which a color separation filter is integrally formed with a solid-state image pickup device, and the other is the frame sequential method which sequentially switches light beams of three primary colors and supplies color information to a solid-state image pickup device. The detailed constructions of endoscopes which respectively use these methods are described in, for example, Japanese Laid-Open Patent No. Sho 51-65962 and Sho 55-54933.

The above-described conventional endoscope will be described with reference to FIG. 9.

Figures 9, 9A:
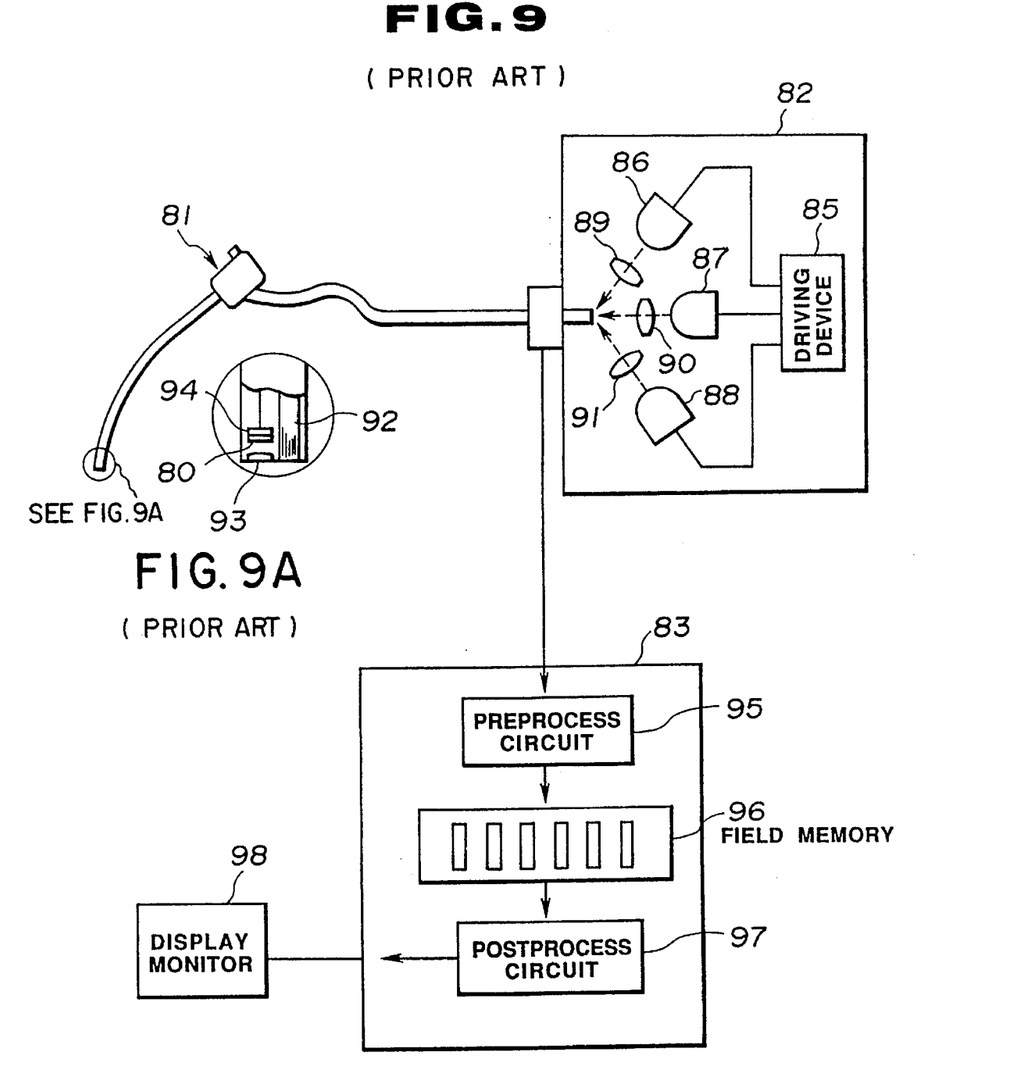
FIGS. 9 and 9A are schematic views showing the construction of a first example of the prior art.

Referring to FIG. 9, lamps 86 to 88 are lighted one-by one by a driving device 85 in a light source device 82, and condenser lenses 89 to 91 are disposed between the lamps 86 to 88 and the back end of a light guide 92 of an endoscope 81 so as to condense light beams from the lamps 86 to 88 onto the back end of the light guide 92. The lenses 89 to 91 each allow only a light beam of a single color, R, G or B, to pass therethrough. As a result, sequential light beams of R, G and B are condensed onto the back end of the light guide 92.

The light guide 92 passes through the endoscope 81, and radiates the R, G and B sequential light beams outward from the leading end of the endoscope 81. The radiated sequential light beams are reflected by an unillustrated object and form an image on the end face of a solid-state image pickup device 80 through an objective lens 93 mounted at the leading end of the endoscope 81. The formed optical image is photoelectrically converted into image pickup signals by the solid-state image pickup device 80, and the image pickup signals are transmitted to a control device 83 through a buffer amplifier 94 and converted into image information by a preprocess circuit 95 in the control device 83.

The R, G and B sequential image information is synchronized by a field memory 96, provided with processing, such as outline emphasis, by a postprocess circuit 97, and output to a display monitor 98, thereby displaying an unillustrated object image. Furthermore, if the transmission of the R, G and B sequential information to the field memory 96 is stopped by the preprocess circuit 95, a freeze image can be obtained.

However, the endoscopic apparatus having the above construction can retain image information for only one frame.

On the other hand, an endoscopic imaging system capable of retaining image information for a plurality of frames is disclosed in, for example, Japanese Laid-Open Patent Nos. Sho 59-69045 and Sho 59-69048 to the inventor of the present invention.

The endoscopic imaging system will be described with reference to FIGS. 10 and 11.

Figure 10:
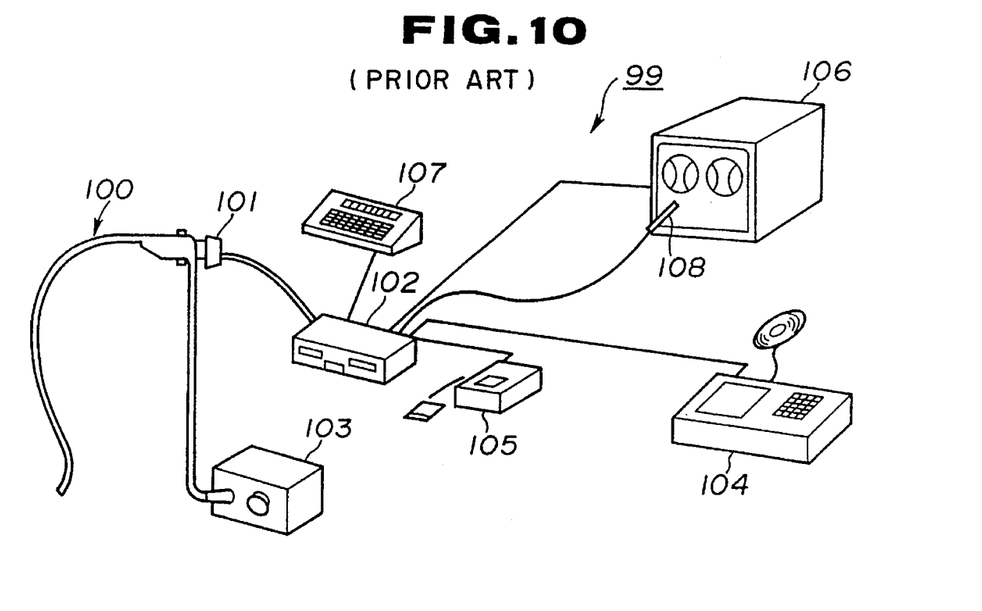
FIG. 10 is an outside view of a second example of the prior art.

Referring to FIG. 10, an endoscopic imaging system 99 is comprised of an endoscope 100, an image pickup camera 101 disposed at the eyepiece of the endoscope 100, a control device 101 for conducting image processing on a picture signal from the image pickup camera 101, a light source device 103 for supplying illumination light to the endoscope 100, a large capacity memory device 104 and a small capacity memory device 105 each capable of storing image information from the control device 102, and a CRT monitor 106 for displaying the image information. Furthermore, a keyboard 107 and a light pen 108 are connected to the control device 102 to designate the contents of image information to be processed.

Figure 11:
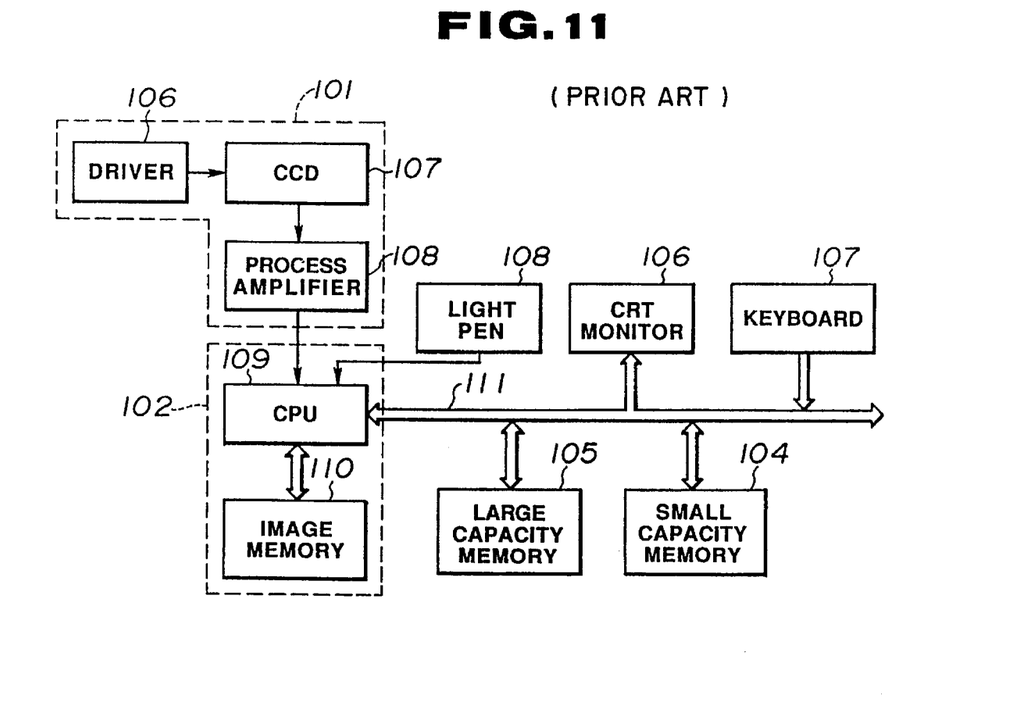
FIG. 11 is a block diagram showing the construction of the second example of the prior art.

In the endoscopic imaging system 99 having such construction, an optical image obtained by the endoscope 100 is photoelectrically converted into image pickup signals by a CCD 107 in the image pickup camera 101, as shown in FIG. 11. The CCD 107 is driven by a driver 106. The generated image pickup signals are converted into picture signals by a process amplifier 108, and transmitted to the control device 102. The transmitted picture signals are converted into digital signals by a CPU 109, and retained in an image memory 110 as image information for one frame.

The CPU 109 outputs the image information to the CRT monitor 106 and retains the image information in the small capacity memory device 104 capable of storing image information for a plurality of frames and the large capacity memory device 105 capable of retaining the image information, both of which are disposed outside of the control device 102, as necessity requires. In response to the operation of the keyboard 107 and the light pen 108, the control device 102 executes various kinds of operations, for example, reading of the image information from the small capacity memory 104 or the large capacity memory 105, synthesizing this image information and image information from the image pickup camera 101 in the image memory 110 of the control device 102, and displaying the synthesized image information on the CRT monitor 106. The image information is transmitted through a bus 111.

However, at least a small capacity memory device and a control device are necessary to store or record and reproduce image information for a plurality of frames, and furthermore, the image information is required to be stored for the colors R, G and B, respectively, in order to achieve high-precision storage. Therefore, at least three signal cables and a plurality of cables for synchronizing signals and control signals are also necessary.

Furthermore, it is necessary to locate a designation device for designating the process contents to the control device, such as a keyboard, near a processing device.

Therefore, the endoscopic imaging system of the prior art requires a large number of complicated peripheral devices in order to store or record and reproduce image information for a plurality of frames.

SUMMARY OF THE INVENTION

It is an object of the present invention to provide an endoscopic apparatus which can store or record and reproduce diversified image information for a plurality of frames without requiring complicated peripheral devices.

An endoscopic apparatus of the present invention comprises an image pickup means for picking up an optical image obtained by an image pickup optical system of an endoscope, a control means for converting and controlling an image pickup signal output from the image pickup means into image information, an illumination means having a light source for supplying illumination light to the endoscope, and a memory means for retaining image information for a plurality of frames of the image information disposed in either the control means or the illumination means.

BRIEF DESCRIPTION OF THE DRAWINGS

FIGS. 1 to 5 illustrate a first embodiment of the present invention.

FIGS. 5 and 5A are perspective views of a second variation of the control device.

FIGS. 6 and 7 illustrate a second embodiment of the present invention.

FIGS. 9 to 11 illustrate the prior art.

DESCRIPTION OF THE PREFERRED EMBODIMENTS

Preferred embodiments of the present invention will now be described with reference to the accompanying drawings.

Figures 1, 1A:
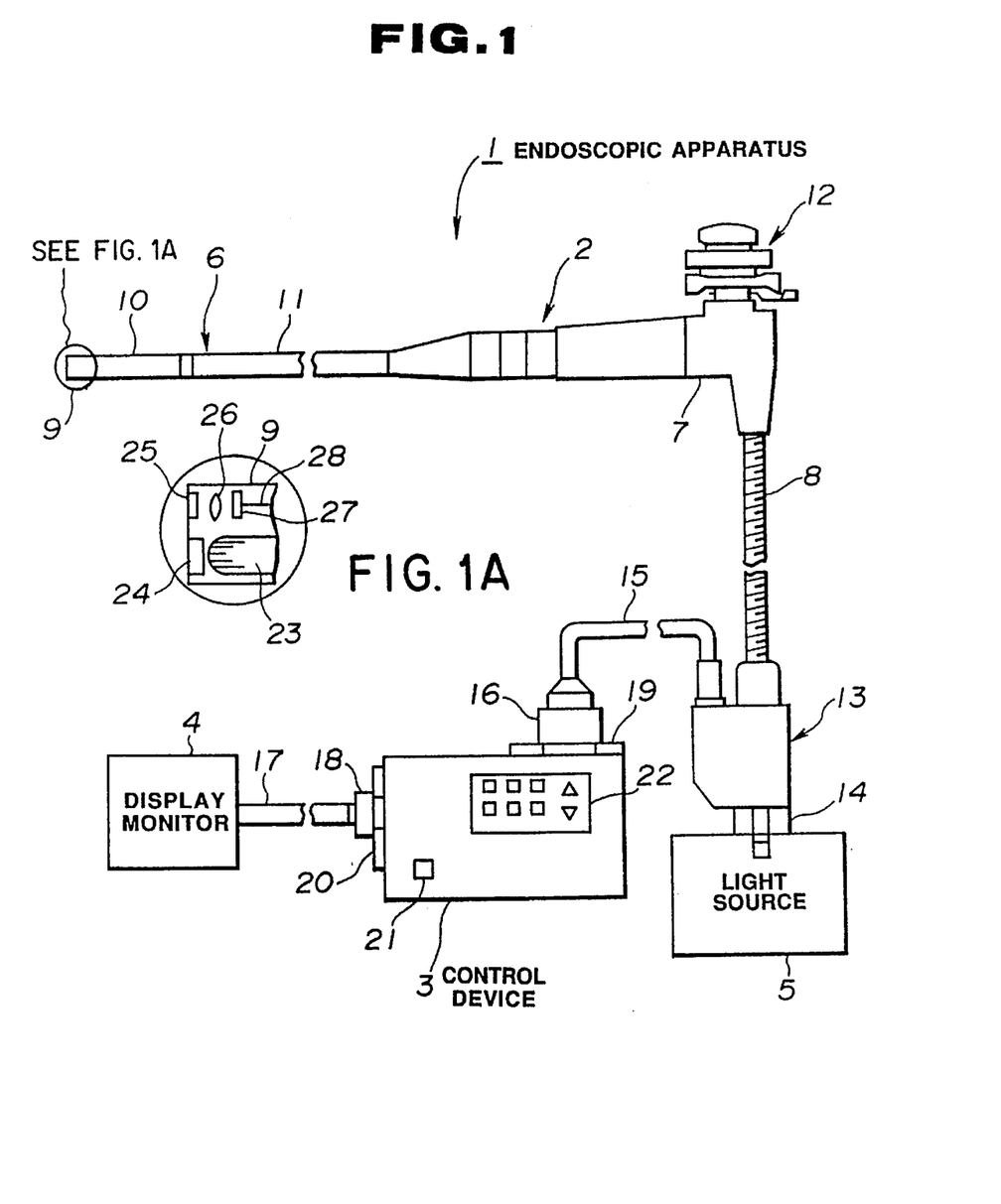
FIGS. 1 and 1A are schematic views showing the configuration of an endoscopic apparatus.

Referring to FIG. 1, an endoscopic apparatus 1 is comprised of an endoscope 2, a control device 3 for processing an image pickup signal transmitted from the endoscope 2, a display monitor 4 for receiving and displaying a picture signal output from the control device 3, and a light source device 5 for supplying illumination light to the endoscope 2.

The endoscope 2 has a long and narrow inserting portion 6, an operating portion 7 connected to the back end of the inserting portion 6, and a universal cord 8 elongated from the side of the operating portion 7.

The inserting portion 6 of the endoscope 2 has a leading portion 9 and a bendable portion 10 next to the leading portion 9. Furthermore, a flexible soft portion 11 is formed next to the bendable portion 10. The bendable portion 10 can be bent in the upward and downward/right and left directions by manipulation of a bending operation knob 12 mounted on the operating portion 7.

A light guide connector (abbreviated as "a LG connector" hereinafter) 13 at the back end of the universal cord 8 is connected to an LG connector receiver 14 mounted to the light source device 5. A signal cord 15 elongated from the side of the LG connector 13 has a signal connector 16 at its back end. A picture connector 18 is disposed at the back end of a picture cable 17 extending from the display monitor 4.

The back end of a light guide 23 passing through the universal cord 8 is disposed in the LG connector 13 so that illumination light can be supplied to the light guide 23 by the light source device 5, and the leading end of the light guide 23 is located behind an illumination lens 24 which is disposed in the leading portion 9 of the endoscope 2 so that the illumination light can be radiated onto an unillustrated object. The leading portion 9 of the endoscope 2 is formed with a monitor window 25 next to the illumination lens 24. Furthermore, an image pickup optical system 26 and a solid-state image pickup device 27 are located behind the monitor window 25, and an unillustrated object image is formed on the surface of the solid-state image pickup device 27. The solid-state image pickup device 27 is connected to an image pickup cable 28 passing through the signal cord 15 and so on, and the back end of the image pickup cable 28 is connected to the signal connector 16.

The control device 3 has a signal connector receiver 19 and a picture connector receiver 20. An image pickup signal which is photoelectrically converted by the solid-state image pickup device 27 can be input by connecting the signal connector 16 to the signal connector receiver 19, while a picture signal can be processed by the control device 3 and output to the display monitor 4 by connecting the picture connector 18 to the picture connector receiver 20. The side of the control device 3 is formed with a SW portion 22 for designating the contents to be processed and a power source SW 21 for controlling ON/OFF of the power supply.

Figure 2:
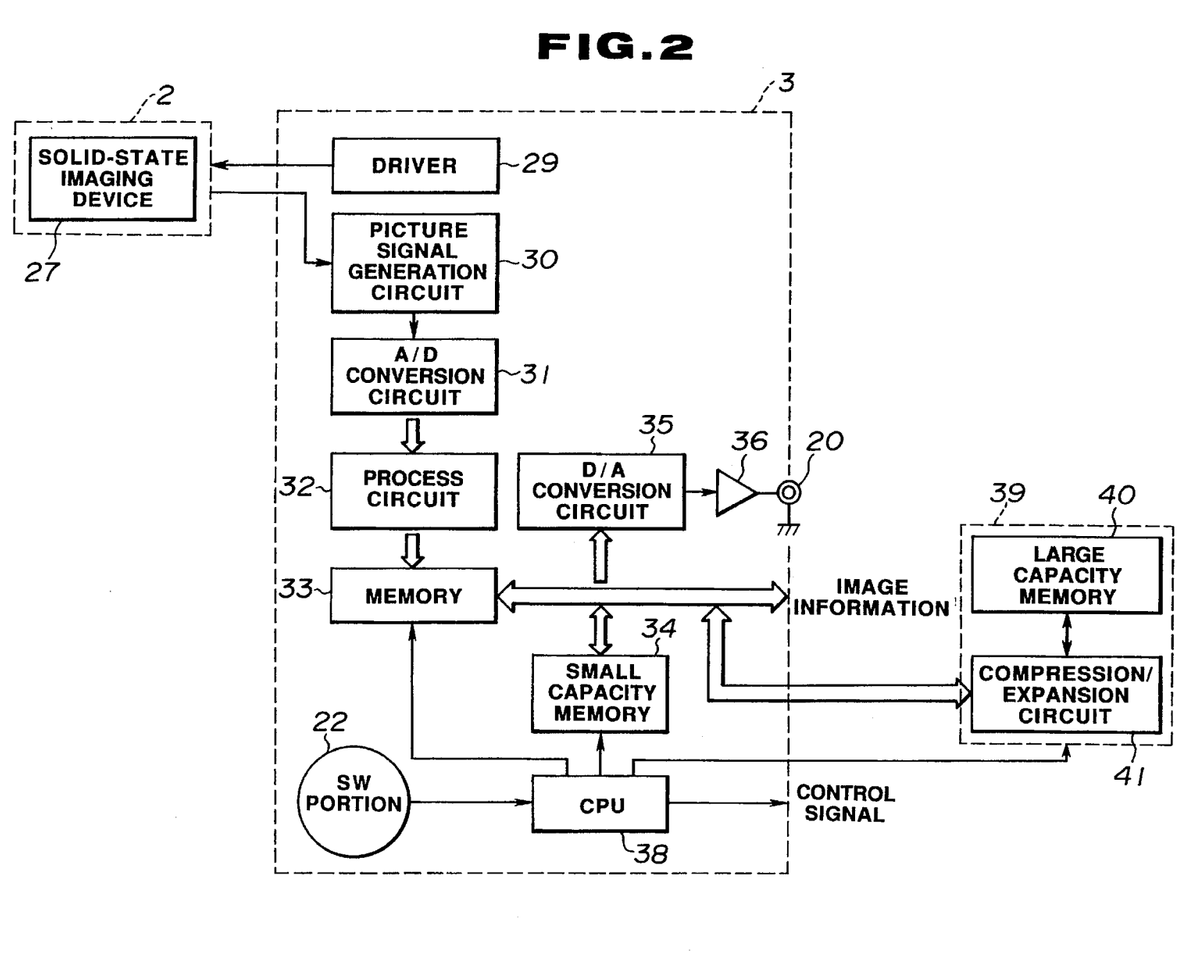
FIG. 2 is a block diagram explaining the construction and operation of a control device.
Figure 3A:
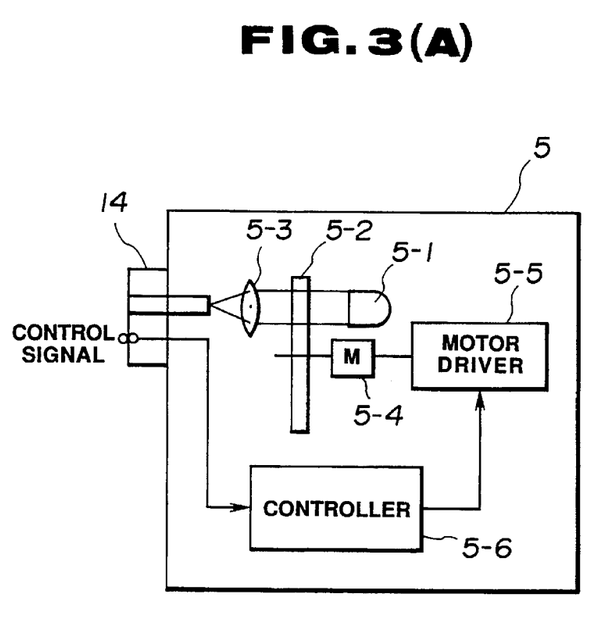
FIGS. 3A and 3B are diagrams showing the construction of a light source device.
Figure 3B:
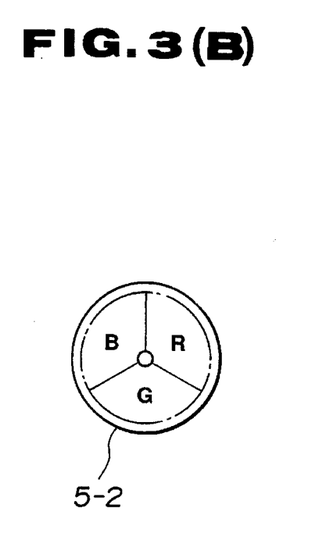

As shown in FIG. 2, the control device 3 is comprised of a driver 29 for driving the solid-state image pickup device 27 in the endoscope 2, a picture signal generation circuit 30 for generating a picture signal based on an image pickup signal which is photoelectrically converted by the solid-state image pickup device 27, an A/D conversion circuit 31 for converting the picture signal from analog to digital, a process circuit 32 for generating image information to be transmitted to a memory 33 capable of storing image information for one frame, based on the picture signal by digital processing, such as interpolation, a small capacity memory 34 capable of storing image information for a plurality of frames and composed of, for example, a semiconductor, a CPU 38 for controlling writing/reading between the memory 33 and the small capacity memory 34, and a D/A conversion circuit 35 for converting the image information from digital to analog so as to generate a video picture signal which is output to the picture connector receiver 20 through an output buffer circuit 36.

If the control device 3 is, as necessity requires, connected to a large capacity memory unit 39 having a compression/expansion circuit 41 for recording image information by compression and reproducing the image information by expansion and a large capacity memory 40 for storing and retaining the image information compressed by the compression/expansion circuit 41, the control device 3 can retain image information. Furthermore, the control device 3 can output a control signal and image information outside in order to transfer the image information to unillustrated devices other than the endoscope 2.

Figure 5:
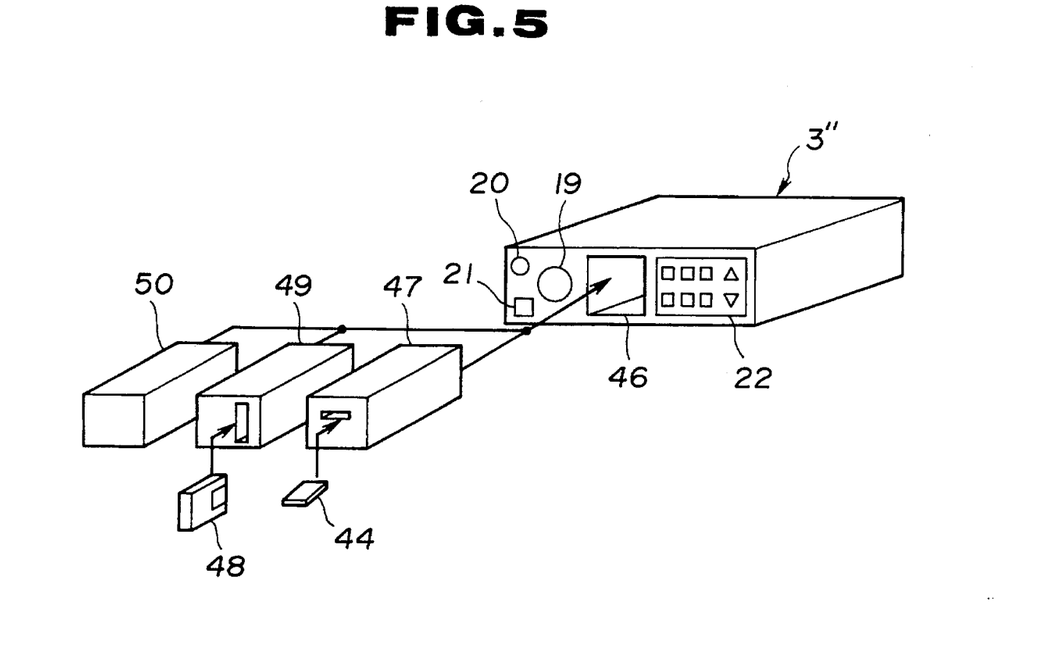

As shown in FIG. 5, the light source device 3 is composed of a light source lamp 5-1 for emitting white light, a rotary filter 5-2 for color-separating the white light from the light source lamp 5-1 to light beams of three primary colors R, G and B, a condenser lens 5-3 for condensing the light beams separated by the rotary filter 5-2 onto the back end of the light guide 23 passing through the endoscope 2, a motor 5-4 for rotating the rotary filter 5-2, a motor driver 5-5 for driving the motor 5-4, and a controller 5-6 for controlling the motor driver 5-5 according to a control signal from the CPU 38 in the control device 3. The signal processing by the control device 3 and the illumination light drive by the light source device 5 are synchronized by a control signal from the CPU 38 in the control device 3.

The endoscopic apparatus 1 thus constructed inputs an image pickup signal from the solid-state image pickup device 27 in the endoscope 2 to the picture signal generation circuit 30 in the control device 3. The picture signal generation circuit 30 generates a picture signal based on the input image pickup signal. The picture signal is converted to a digital signal by the A/D conversion circuit 31, provided with digital processing, for example, tone adjustment and outline emphasis, by the process circuit 32, and transferred as image information to the memory 33. The CPU 38 stores image information for one frame in the memory 33, and stores image information for a plurality of frames in the small capacity memory 34 in response to the operation of the SW portion 22. Furthermore, the CPU 38 transfers the past image information read from the small capacity memory 34 to the memory 33 in response to the operation of the SW portion 22, creates synthesis/comparison image information obtained by synthesizing or comparing the past image information and the present image information in the memory 33, and outputs the synthesis/comparison image information to the picture connector receiver 20. Furthermore, the CPU 38 stops writing to the memory 33 in response to the actuation of the SW portion 22, thereby outputting freeze image information to the picture connector receiver 20.

Therefore, the connection of the picture connector 17 to the picture connector receiver 20 enables the display monitor 3 to display not only an image of an unillustrated object which is being picked up at present but also various kinds of images.

According to the endoscopic apparatus of the first embodiment, it is possible to obtain various images other than an image of the object, which is being picked up at present, in a simple construction without requiring any peripheral device. If the endoscopic apparatus is used for diagnosis or the like, since it is compact and thus excellent in portability, the operator can immediately and visually explain the result of the diagnosis to the patient, and easily obtain understanding of future treatment from now on from the patient. Furthermore, since the construction of the endoscopic apparatus is on a small scale, the storage of image information for a plurality of frames can be achieved less expensively than the conventional apparatus.

Figure 4:
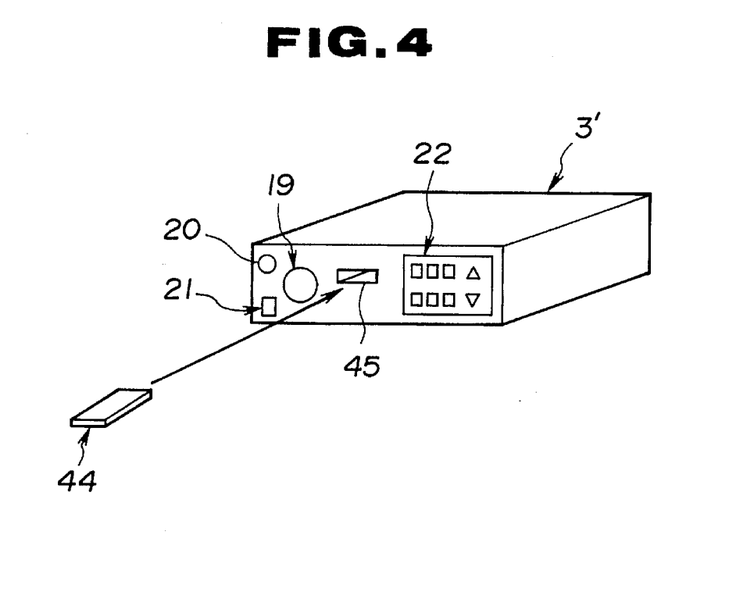
FIG. 4 is a perspective view of a first variation of the control device.

Although the control device 3 has the small capacity memory 34 composed of a semiconductor in the first embodiment, the present invention is not limited to the first embodiment. For example, as shown in FIG. 4, a control device 3' may use an IC card 44 as a small capacity memory and be formed with an IC card insertion opening 45 in which the IC card 44 can be inserted. Furthermore, as shown in FIG. 5, a control device 3" may use a memory unit as a small capacity memory, for example, an IC card memory unit 47 in which an IC card 44 is inserted, an optical disk memory unit 49 in which an optical disk 48 is inserted, or a magnetic disk, memory unit 50, and be formed with a memory inserting receptacle 46 in which any one of the above memory units can be mounted.

Although the light source device supplies sequential light beams of R, G and B through the rotary filter, it may supply sequential light beams R, G and B, for example, by lighting lamps for emitting R, G and B light beams in turn as described in the prior art shown in FIG. 9.

An endoscopic apparatus according to a second embodiment of the present invention will now be described.

Figure 6:
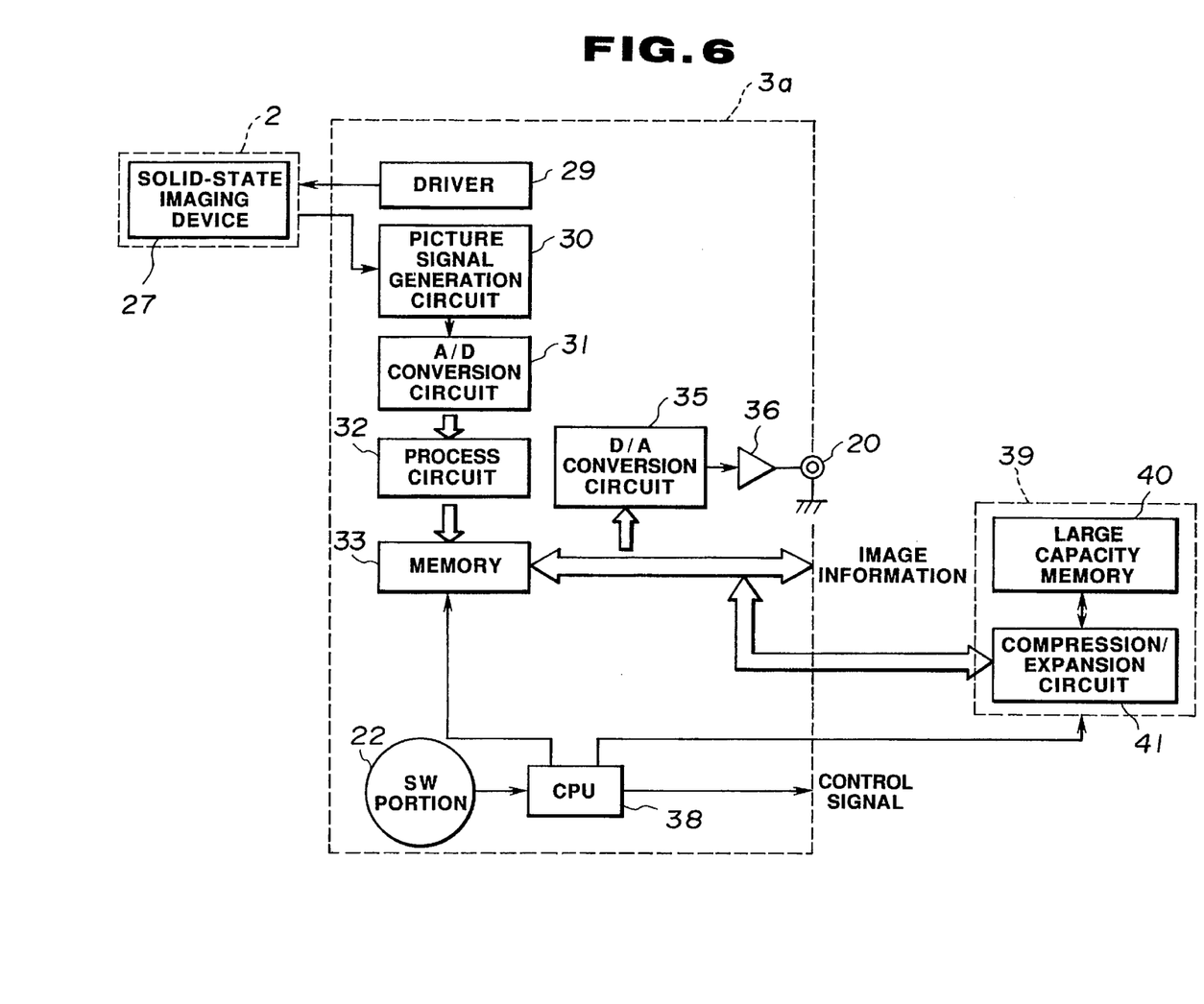
FIG. 6 is a block diagram explaining the construction and operation of a control device.

As shown in FIG. 6, a control device 3a in the endoscopic apparatus in the second embodiment has almost the same construction as that of the control device 3 in the first embodiment. In other words, the small capacity memory 34 in the control device 3 is omitted herein. Since other components of the control device 3a are the same as those in the control device 3, they are denoted by the same numerals and the description of them is omitted.

Figure 7:
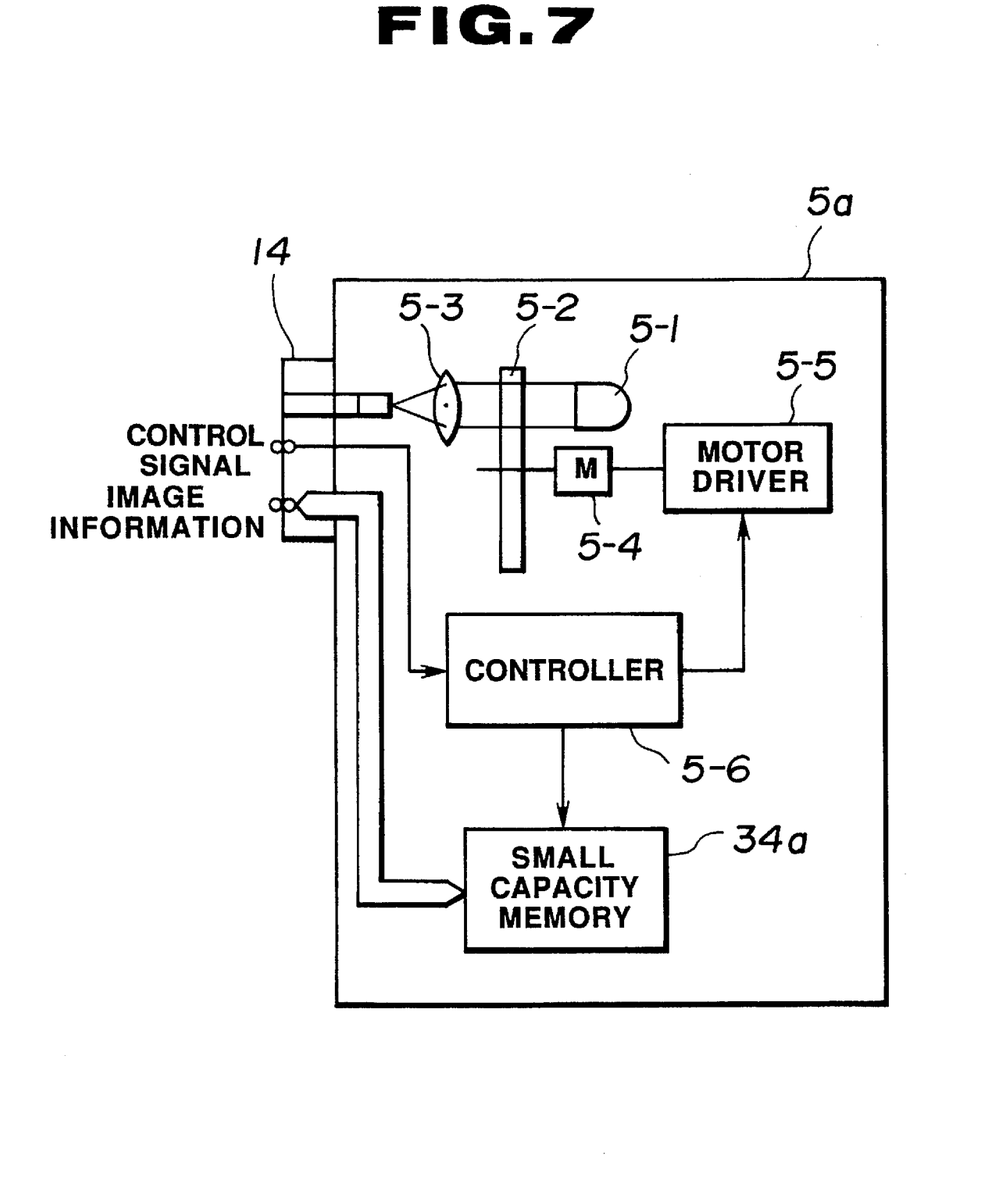
FIG. 7 is a block diagram showing the construction of a light source device.

Referring to FIG. 7, a light source device 5a in the endoscopic apparatus of the second embodiment is, in the same manner as in the first embodiment, composed of a light source lamp 5-1 for emitting white light, a rotary filter 5-2 for color-separating the white light from the light source lamp 5-1 to light beams of three primary colors R, G and B, a condenser lens 5-3 for condensing the light beams separated by the rotary filter 5-2 onto the back end of a light guide 23 passing through an endoscope 2, a motor 5-4 for rotating the rotary filter 5-2, a motor driver 5-5 for driving the motor 5-4, and a controller 5-6 for controlling the motor driver 5-5 according to a control signal from a CPU 38 in the control device 3a. Furthermore, the light source device 5a has a small capacity memory 34a composed of a semiconductor capable of inputting and storing image information from the control device 3a, thereby having the controller 5-6 retain the image information in the small capacity memory 34a.

Other construction and operation are the same as those of the first embodiment.

Since the small capacity memory 34a is disposed in the light source device 5a in which extra space is easily secured in connection with thermal design, it is possible to make the control device 3a compact or to add image processing circuits other than the above ones in the control device 3a.

Other advantages of the second embodiment are the same as those of the first embodiment.

Although the light source device 5a includes the small capacity memory 34a composed of a semiconductor in the second embodiment, the present invention is not limited to the second embodiment. For example, the control device may use an IC card as a small capacity memory and be formed with an IC card insertion opening in which the IC card can be inserted. Furthermore, the control device may use a memory unit as a small capacity memory, for example, an IC card memory unit in which an IC card is inserted, an optical disk memory unit in which an optical disk is inserted, or a magnetic disk memory unit, and be formed with a memory inserting portion in which one of the above memory units can be mounted.

An endoscopic apparatus of a third embodiment will now be described.

The endoscopic apparatus of the third embodiment has almost the same construction as that of the first embodiment. In other words, in a control device 3b shown in FIG. 8, a small capacity memory 34b composed of a semiconductor is located in the stage previous to a process circuit 32 for performing digital processing, and a CPU 38 retains picture signals generated by an A/D conversion circuit 31 before digital processing, such as tone adjustment or outline emphasis, in the small capacity memory 34b. Furthermore, the control device 3b can output control signals, picture signals before digital processing and image information after digital processing outside in order to transfer information to unillustrated devices, and be connected to a large capacity memory unit 39 for retaining picture signals before processing.

Other components are the same as those in the first embodiment and denoted by the same numerals, and thus the description of the components is omitted.

Figure 8:
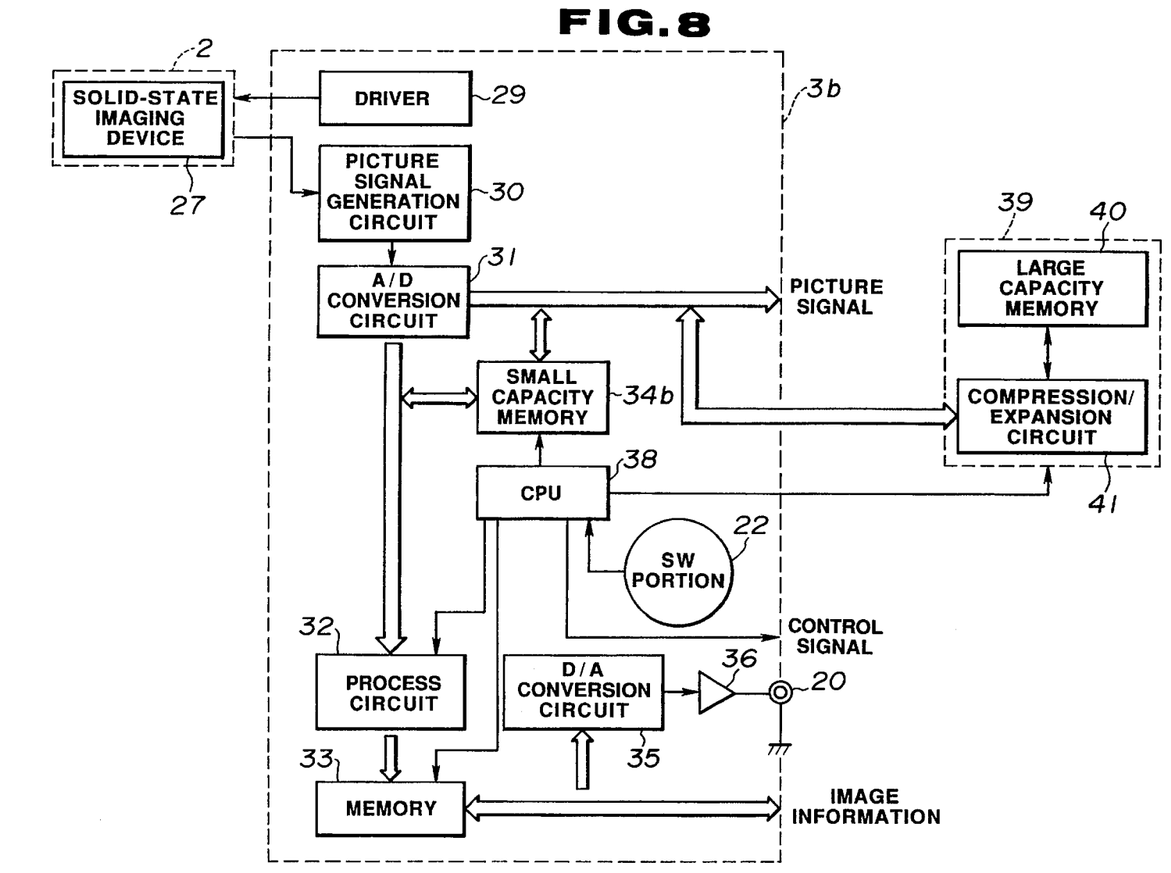
FIG. 8 is a block diagram explaining the construction and operation of a control device according to a third embodiment of the present invention.

In the endoscopic apparatus of the third embodiment having such construction, since processing, such as interpolation, is not conducted on picture signals, the amount of information corresponding to the picture signals is smaller than that of signals on which processing like interpolation is conducted. Therefore, the small capacity memory 34 can store information for more frames. Furthermore, since the digital processing, such as tone adjustment and outline emphasis, is carried out in the process circuit 32, the conditions of picture signals stored in the small capacity memory 34 without being digitally processed can be always kept constant, and diversified digital processes can be carried out by using unillustrated external devices.

Other operations and advantages are the same as those of the first embodiment.

Although the control device 3b of the third embodiment includes the small capacity memory 34b composed of a semiconductor, the present invention is not limited to the third embodiment. For example, the control device may use an IC card as a small capacity memory and be formed with an IC card insertion opening in which the IC card can be inserted in the same manner as in the first embodiment. Furthermore, the control device may have a memory unit as a small capacity memory, for example, an IC card memory unit in which an IC card is inserted, an optical disk memory unit in which an optical disk is inserted, or a magnetic disk memory unit, and a memory inserting portion in which one of the above memory units can be mounted.

In addition, although the endoscopic apparatus of the present invention is constituted by an endoscope, a control device and a light source device and a small capacity memory is disposed in either the control device or the light source device, the present invention is not limited to the above embodiments. For example, the endoscopic apparatus may be constituted by an endoscope and a light source control device including a light source and having the same functions as those of the control device shown in the first embodiment, in which a small capacity memory is additionally mounted.

It will be apparent that various modifications of the present invention can be made without departing from the spirit and scope of the invention.

What is claimed is:

1. An endoscopic apparatus, comprising:

image pickup means for picking up an optical image obtained by an imaging optical system in an endoscope;

illumination means including a light source for supplying illumination light to said endoscope; and control means for controlling an image pickup signal output from said image pickup means, said control means including an analog-to-digital converter for converting said image pickup signal into digital image information, wherein said control means further including memory means for digitally storing said digital image information for a plurality of images consisting of continuous multiple frames of said digital image information recorded in a predetermined time interval; and wherein said memory means includes a plurality of detachable memory-type adaptor devices, each said memory-type adaptor device being insertable into a single common receptacle in said control means, said memory-type adaptor devices being adapted to house memory devices having different formats, respectively.

2. An endoscopic apparatus according to claim 1, wherein said illumination means sequentially supplies light beams of three primary colors R, G and B to said endoscope.

3. An endoscopic apparatus according to claim 1, wherein said control means consists of digital conversion means for converting the image pickup signal into a digital image signal, and digital processing means for digitally processing the digital image signal from said digital conversion means so as to generate said digital image information.

4. An endoscopic apparatus according to claim 2, wherein said illumination means supplies the light beams to said imaging optical system in said endoscope by sequentially passing white light from a white light source through a filter having permeability for light beams of R, G and B.

5. An endoscopic apparatus according to claim 2, wherein said illumination means supplies the light beams to said imaging optical system in said endoscope by sequentially lighting three light sources for emitting light beams of three primary colors R, G and B.

6. An endoscopic apparatus according to claim 2, wherein said control means consists of digital conversion means for converting said image pickup signal from said image pickup means corresponding to the light beams supplied by said illumination means into a digital image signal, and digital processing means for digitally processing the digital image signal from said digital conversion means so as to generate said digital image information.

7. An endoscopic apparatus according to claim 3, wherein said memory means is a semiconductor memory for storing the digital image signal from said digital conversion means.

8. An endoscopic apparatus according to claim 3, wherein said memory means is a magnetic recording medium for storing the digital image signal from said digital conversion means.

9. An endoscopic apparatus according to claim 3, wherein said memory means is an optical recording medium for storing the digital image signal from said digital conversion means.

10. An endoscopic apparatus according to claim 3, wherein said memory means is a semiconductor memory for storing said digital picture signal from said digital processing means.

11. An endoscopic apparatus according to claim 3, wherein said memory means is a magnetic recording medium for storing said digital picture signal from said digital processing means.

12. An endoscopic apparatus according to claim 3, wherein said memory means is an optical recording medium for storing said digital picture signal from said digital processing means.

13. An endoscopic apparatus according to claim 6, wherein said memory means is a semiconductor memory for storing the digital image signal from said digital conversion means.

14. An endoscopic apparatus according to claim 6, wherein said memory means is a magnetic recording medium for storing the digital image signal from said digital conversion means.

15. An endoscopic apparatus according to claim 6, wherein said memory means is an optical recording medium for storing the digital image signal from said digital conversion means.

16. An endoscopic apparatus according to claim 6, wherein said memory means is a semiconductor memory for storing said digital picture signal from said digital processing means.

17. An endoscopic apparatus according to claim 6, wherein said memory means is a magnetic recording medium for storing said digital picture signal from said digital processing means.

18. An endoscopic apparatus according to claim 6, wherein said memory means is an optical recording medium for storing said digital picture signal from said digital processing means.

19. An endoscopic apparatus comprising:

image pickup means for picking up an optical image obtained by an imaging optical system in an endoscope;

illumination means including a light source for supplying illumination light to said endoscope; and control means for controlling an image pickup signal output from said image pickup means, said control means including an analog-to-digital converter for converting said image pickup signal into digital image information, and said control means further including memory means for digitally storing said digital image information for a plurality of images, and an output terminal being able to output said digital image information from said memory means wherein said memory means includes a plurality of detachable memory-type adaptor devices, each said memory-type device being insertable into a single common receptacle in said control means, said memory-type adaptor devices being adapted to house memory devices having respectively different formats; and external memory means connected to said output terminal, said external memory means having larger storage capacity than that of said memory means.

* * * * *